United States Patent [19]

Baenens et al.

[11] 4,183,810
[45] Jan. 15, 1980

[54] PROCESS AND DEVICE FOR THE BIOLOGICAL PURIFICATION OF WASTE WATER

[75] Inventors: Victor E. A. Baenens; Jan A. L. Thissen, both of Geleen, Netherlands

[73] Assignee: Stamicarbon, B.V., Geleen, Netherlands

[21] Appl. No.: 905,172

[22] Filed: May 11, 1978

[30] Foreign Application Priority Data

May 17, 1977 [NL] Netherlands ................. 7705427

[51] Int. Cl.² .................................................. C02C 5/10
[52] U.S. Cl. ............................................ 210/11; 210/16; 210/96.1; 210/DIG. 28
[58] Field of Search .............. 210/16, DIG. 28, 96 R, 210/18, 3–7, 11, 195 R, 202; 23/230 R, 230 B

[56] References Cited

U.S. PATENT DOCUMENTS 3,964,998  6/1976  Barnard ................. 210/DIG. 28
4,056,465  11/1977  Spector ................. 210/DIG. 28

FOREIGN PATENT DOCUMENTS 2204576  5/1974  France ................. 210/DIG. 28
47-17266  9/1972  Japan ................. 210/DIG. 28
51-8754  1/1976  Japan ................. 210/DIG. 28

OTHER PUBLICATIONS

Gool H. Van, "Purification of Industrial Waters"; Centre Belge d'Etude et de Documentation des Eaux, Jun.-Jul. 1976, #391–392, pp. 265–279.
Andrews et al.; "Progress in Water Technology", vol. 6 (1973), pp. 124–130.

Primary Examiner—Benoit Castel
Attorney, Agent, or Firm—Cushman, Darby & Cushman

[57] ABSTRACT

Process and apparatus for the biological purification of waste water containing nitrogen compounds. This purification is effected in one or more steps, in the last of which the waste water is denitrified, while additional BOD is added to this step. The supply of BOD to this step is controlled automatically through the continuous analysis of the nitrite-plus-nitrate content in either this step or the discharge from this step.

6 Claims, 4 Drawing Figures

PROCESS AND DEVICE FOR THE BIOLOGICAL PURIFICATION OF WASTE WATER

BACKGROUND AND SUMMARY OF THE INVENTION

The present invention relates to a new and novel process for the biological purification of waste water containing nitrogen compounds, in one or more steps, in the last of which the waste water is denitrified, with additional BOD being added to this denitrification step.

Waste water contains not only organic compounds, but also nitrogen compounds, such as, e.g., ammonia and nitrate. These compounds must be removed thoroughly from the waste water. The purification is effected biologically by means of bacteria. To accomplish this, use is made of the biological processes of denitrification and optionally nitrification, that are parts of the nitrogen cycle in nature. The denitrification process takes place in an anaerobic atmosphere, i.e., poor in oxygen, and it requires organic material. The organic material is expressed as biological oxygen demand, or as it is commonly referred, BOD. This is the amount of oxygen consumed by the bacteria when the organic material is oxidized by the bacteria.

In normal purifying installations this oxidation is effected by means of oxygen in the air, which is usually mechanically dissolved in the water. If no dissolved oxygen is present in the water during the denitrification reaction, the oxygen from the nitrate or nitrite is used as the oxidizing agent for the organic material. In the nitrification reaction ammonia is oxidized biologically into nitrite or, further, into nitrate. This reaction is effected by other bacteria than those effecting the denitrification reaction. Moreover, the atmosphere is rich in oxygen, i.e., aerobic. Hence, the entire purifying process must be effected in steps.

The simplest embodiment is a single denitrification in which waste water containing only nitrates as nitrogen compounds is purified in the above way.

If the impurities in the nitrogen-containing waste water mainly consist of nitrogen, both in the reduced and in the oxidized form, with comparatively little biologically degradable material, use is mostly made of a nitrification step followed by a denitrification step.

A third step may be used if the waste water contains both nitrogen compounds and biologically degradable organic material. This embodiment has been described in Netherlands Patent Application No. 72.14701. According to this embodiment, the first step is a denitrification step to make the BOD and nitrite plus nitrate in the waste water react. Next there is an oxidation step in which ammonia is oxidized into nitrite or nitrate. After these two steps, only nitrate and nitrite remain, which have to be removed in the third step, the second denitrification. The removal of these nitrates and nitrites will require BOD which must be added separately.

As very stringent demands are made on waste water discharged into surface water, virtually all nitrite and nitrate must be removed in the final step. This may be accomplished by adding excess BOD. One disadvantage of adding excess BOD is that, after the final step which is the (second) denitrification, the water will again contain BOD. This is not acceptable as the discharged water should not contain BOD. Therefore, a last or oxidizing step is necessary. By following this process, the requirements for discharged waster water can be met at any rate of treatment.

Obviously, the last oxidizing step depends on the amount of excess BOD present in the final denitrification step. Prior to this invention, it has not been possible to control the addition of BOD in this step to meet the requirements for discharging nitrite, nitrate and BOD in the discharged treated waste water without omitting the last, oxidizing step.

OBJECT OF THE INVENTION

The object of the invention is to provide a control system for the supply of BOD in the final denitrification step so that the requirements for discharging nitrites, nitrates, and BOD in the discharged treated waste water are met without the need for a last oxidizing step.

When this control system was being designed, a number of problems were encountered. These included:

(1) measurement of the total of nitrite and nitrate. In the oxidation of $NH_4^+ - N$, both nitrite and nitrate may form. These components can be used both as starting materials for the denitrification reaction. Another possibility is that nitrite is formed from nitrate in partial denitrification. In general, however, the nitrite content is low compared to the nitrate content, $NO_2^- - N < 10\%$ of $NO_3^- - N$;

(2) the low concentration range of the measurement, viz. the effluent concentration of 0-10 mg/l $(NO_2^- + NO_3^-) - N$. Also, low concentrations have to be measured depending on the discharging requirements that have to be met;

(3) measurement in industrial waste water which contains not only the components to be measured, but also a great many other substances in ever varying concentrations. Hence, the detection must be highly specific; and (4) the necessity of continuous measurement. The automatic feed of a process flow generally requires continuous measurement, unless the process parameters are quite constant and a slight variation of the flow to be controlled does not materially affect the process. In this situation, more or less frequent manual analysis and adjustment of the feed flow may suffice, but this is definitely not acceptable in the present situation where it is waste water from a chemical industry that must be treated and discharged.

In the process according to the present invention, the BOD supply to the final denitrification treatment step is controlled by means of continuous analysis of the nitrite-plus-nitrate content in this denitrification step or in the discharge from this step. This analysis comprising the following steps:

(a) withdrawal and filtration of a continuous sample flow of the waste water;

(b) preferential conversion of all nitrite into nitrate or of all of the nitrate into nitrite;

(c) preferential spectrophotometric determination of the nitrite or nitrate content;

(d) transformation of the resulting signal into a signal to the BOD supply by means of a proportionally integrating controller; and (e) regular zero adjustment of the analysis equipment, while the measuring equipment is bridged for at least part of the time required for the adjustment and the BOD supply during this period is kept constant at the last-measured value.

The process is preferably so effected that, from the start of the zero adjustment, the BOD supply is controlled by way of the analysis equipment for part of the delay time of the analysis equipment, after which the equipment is bridged, at least, for a time equal to the time required for the zero adjustment.

One advantage of this process over the known process is that the second oxidizing step can be omitted. This results in a substantial saving in capital investment. Another advantage of this process is that it makes possible the reduction of the required amount of BOD to a minimum amount which means the variable cost entailed in the purification can be kept as low as possible. All this can be done without discharging more nitrates, nitrites and BOD in the discharged treated waste water into the surface water than are permitted and necessary.

Netherlands Patent Application No. 7,214,701 discloses the need to control BOD supply with reference to the total content of nitrite plus nitrate into the discharge from the second denitrification step. However, no indication whatsoever is given about the nature of this control. More importantly, this Netherlands Patent Application recites need for aeration after the second denitrification which means that excess BOD was added to the second denitrification step. The mere fact this second oxidizing step is said to be necessary in this Netherlands Patent Application implies that a control system according to the present invention was not contemplated or considered.

The system of the present invention is preferably controlled with reference to an analysis of the nitrite content preceded by preferential reduction of nitrate into nitrite, e.g., by means of an alkaline solution of hydrazine sulphate in the presence of a copper catalyst (copper sulphate). Accurate determination of the nitrite content is then possible after reaction with a reagent that preferentially reacts with nitrite and subsequent spectrophotometric determination. See, e.g. 'Standard Methods for the examination of water and waste water' (12th ed.), American Public Health Association, Inc.

DESCRIPTION OF THE DRAWINGS AND DETAILED DESCRIPTION OF THE INVENTION

The invention will be further elucidated with reference to the drawing, where

Figure 1:
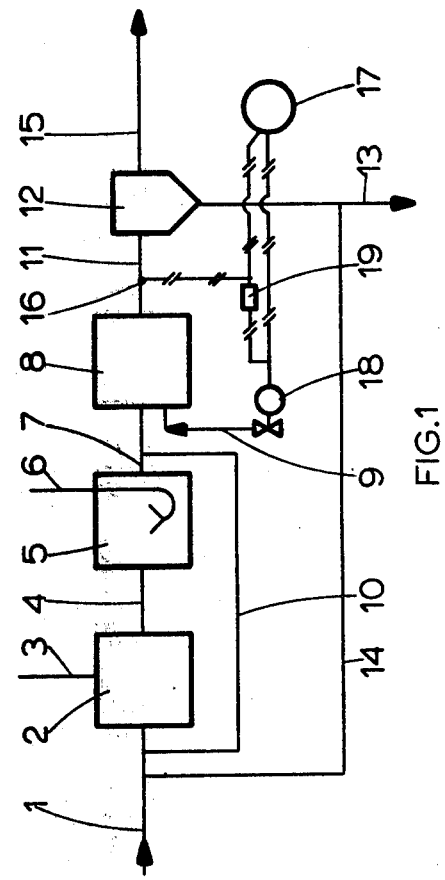
FIG. 1 shows an embodiment of the process according to the present invention.

FIG. 1 shows a diagram for the purification of waste water. Waste water to be treated and containing organic impurities in addition to nitrogen compounds is supplied through conduit 1. In the first denitrification zone 2 nitrate nitrogen is reduced to molecular nitrogen under anaerobic conditions with the organic impurities acting as oxygen acceptor; naturally another oxygen acceptor may be used, but the effect is only negative. The gaseous nitrogen leaves 2 through discharge 3. The denitrified water flows through conduit 4 to nitrification zone 5. Air or another gas containing molecular oxygen is passed in through conduit 6. Not only is ammonium nitrogen oxidized to nitrate nitrogen in 5, but also any biologically degradable material present is oxidized to carbon dioxide and water. Conduit 7 connects the nitrification zone with the second denitrification zone 8. 8 is fed with an oxygen-acceptor, which is preferably free of ammonium nitrogen, through 9. This oxygen-acceptor may be, e.g., methanol, hydrogen gas, or a solution of organic acids, such as waste water from a process for the preparation of cycloalkanones and/or cycloalkanols by oxidation of a cycloalkene with molecular oxygen. Part of the water treated in 5 is returned to 2 through conduit 10. Conduit 11 transports the water treated in 8 to sludge-settling zone 12. Part of the settled sludge is removed through 13 and part is pumped back to 2 through return conduit 14. The treated waste water leaves the installation through conduit 15.

Conduit 11, or alternately second denitrification zone 8, incorporates measuring point 16 of nitrate analyzer 17. The supply of oxygen-acceptor to 8 through 9 is so controlled by valve 18 that the nitrate content in the effluent is minimal. The oxygen-acceptor will have to be reactive, as the effluent will otherwise contain unconverted oxygen-acceptor. Examples of suitable oxygen-acceptors are organic substances that can readily be oxidized biologically, such as methanol and the like. It will then be possible to obtain an effluent that is virtually free of nitrogen compounds and organic substances. During the zero adjustment, which may be done automatically, 17 is bridged by way of 19.

Figure 2:
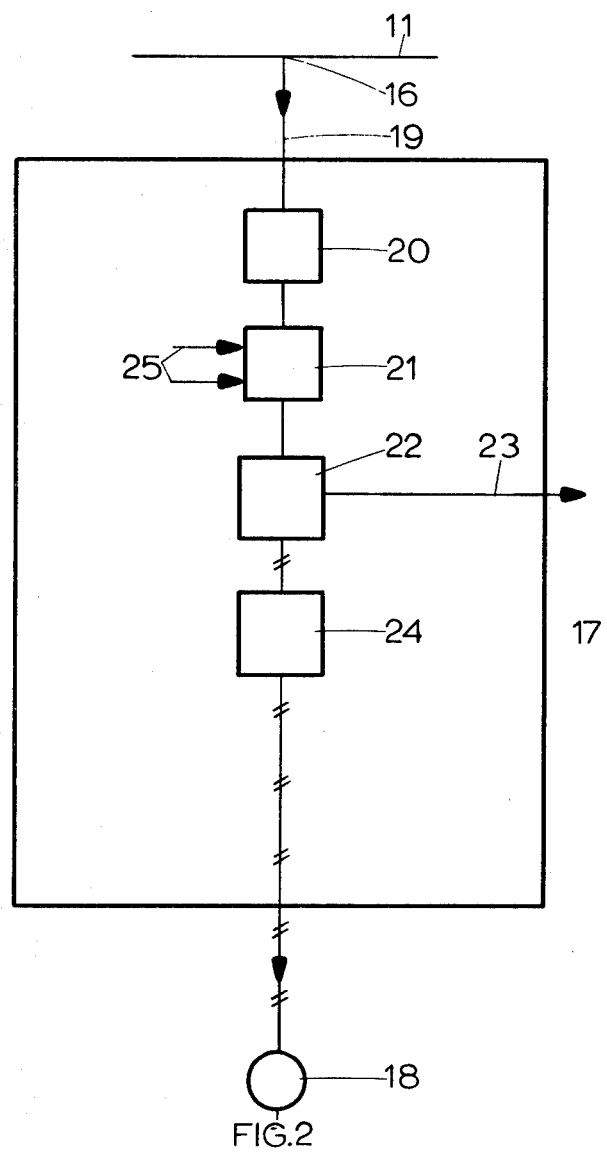
FIG. 2 shows a possible embodiment of part of FIG. 1.

FIG. 2 shows a diagram of nitrate analyzer 17 in FIG. 1. A sample flow consisting of waste water and suspended sludge flows continuously from measuring point 16 through conduit 19 to nitrate analyser 17. This analyser comprises a continuous filter 20, e.g., a ribbon filter. After this filtration, the clear liquid is treated in 21 with reagents required for the preferential determination of nitrite plus nitrate. These reagents are supplied through 25. The liquid thus treated flows to spectrophotometer 22, where the total content of nitrite plus nitrate is determined continuously. The measured samples leave the analysis equipment through 23, e.g., for purification and discharge.

The signal of the spectrophotometer is transmitted to the proportionally integrating controller 24. Here the signal is converted into a signal to the BOD supply, which is such that the nitrite-plus-nitrate content in the effluent from the second denitrification step is kept at or below a preset level.

EXAMPLES

Figure 3:
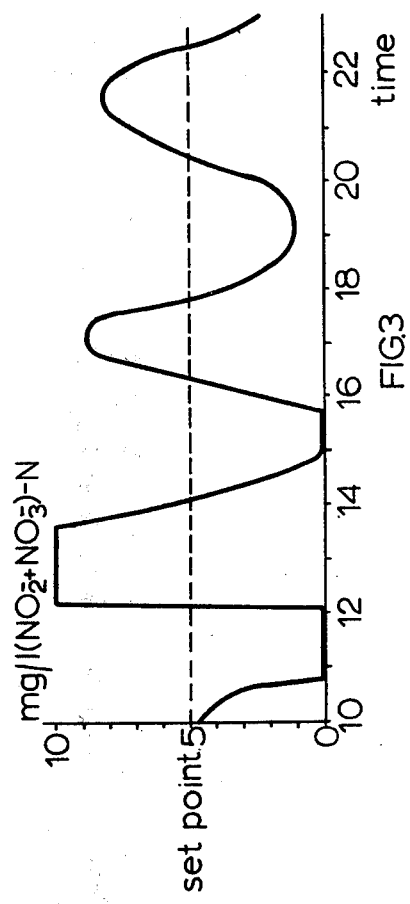
FIGS. 3 and 4 show two graphs in which the nitrogen content of the effluent of a purifying installation is plotted as a function of time.

FIG. 3 shows the results of a 13-hours equipment with the above-described process, but without the use of the bridge. It is clear that the BOD-supply is fully upset after the zero-adjustment and fluctuates strongly around the set point, while the total content of nitrite plus nitrate highly exceeds the permitted maximum.

Figure 4:
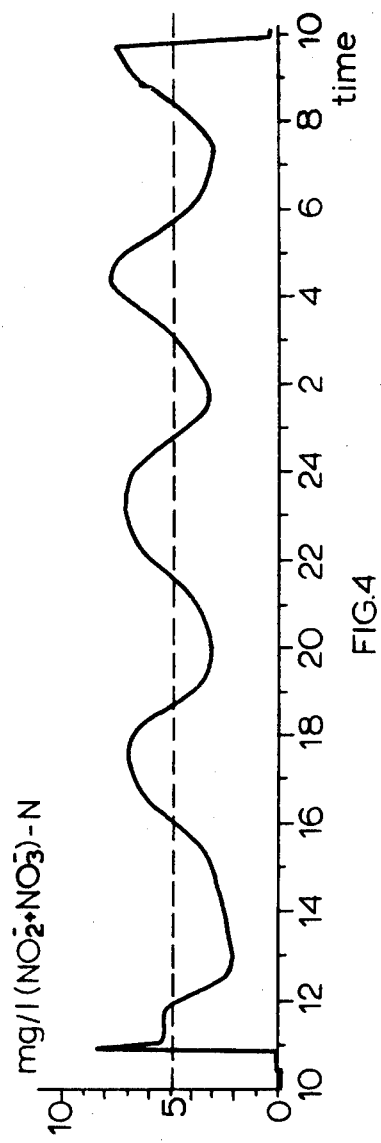

FIG. 4 shows the result of an experiment in which the bridge is used. It is evident that no strong fluctuations occur in this experiment, so that peak discharges can be avoided.

What is claimed is:

1. Process for the biological purification of waste water containing nitrogen compounds wherein said biological purification process comprises at least one step and in which the waste water is denitrified in the final step of said biological purification while additional BOD is added to this final denitrification step, and wherein the BOD supply to said final denitrification step is controlled automatically by means of continuous analysis of the nitrite-plus-nitrate content in said final denitrification step or in the discharge from this step, said continuous analysis comprising the steps of, (i) withdrawing and filtering of a continuous sample flow of the waste water;

(ii) preferential converting of all nitrite into nitrate or all of the nitrate into nitrite;

(iii) preferential spectrophotometric determining of the nitrite or nitrate content;

(iv) transforming of the resulting signal into a signal to the BOD supply by means of a proportionally integrating controller; and (v) zero adjusting of the analysis equipment on a regular basis during at least part of the time required for said adjusting, said analysis equipment is bridged while the BOD supply is kept at a rate constant with the last predetermined value.

2. Process of claim 1, wherein from the start of the zero adjustment, the BOD supply is controlled by way of the analysis equipment for part of the delay time of the equipment, after which the equipment is bridged at least for a time equal to the time required for the zero adjustment.

3. Process of claim 1 or 2, wherein all nitrate present is preferentially reduced to nitrite.

4. Process according to claim 1, wherein the waste water is nitrified in a first step and denitrified in a following step.

5. Process according to claim 4, characterized in that the waste water is first denitrified, then nitrified, and finally denitrified again.

6. Apparatus for the purification of waste water comprising a first denitrification device having a plurality of fluid conduit means, a nitrification device, with a plurality of fluid conduit means connecting said nitrification device to said first denitrification device and to a second denitrification device with a plurality of fluid conduit means, with said second denitrification device provided with conduit means to BOD supply means, said BOD supply means provided with controlling means and means for analyzing the nitrate-plus-nitrite content, said analysis means comprising filtering means, means for supplying reagents to the filtered liquid, means for spectrophotometering the nitrite plus nitrate content of the liquid, and integrating controller means for receiving said spectrophotometric analysis.

* * * * *